United States Patent [19]
Felix

[11] Patent Number: 5,087,329
[45] Date of Patent: Feb. 11, 1992

[54] PROCESS FOR SEPARATING PENTAFLUOROETHANE FROM A MIXTURE OF HALOGENATED HYDROCARBONS CONTAINING CHLOROPENTAFLUOROETHANE

[75] Inventor: Vinci M. Felix, Kennett Square, Pa.

[73] Assignee: E. I. Du Pont de Nemours and Company, Wilmington, Del.

[21] Appl. No.: 714,374

[22] Filed: May 16, 1991

[51] Int. Cl.$^5$ .................... B01D 3/40; C07C 17/38
[52] U.S. Cl. ........................ 203/67; 203/99; 570/178
[58] Field of Search ............ 203/67, 99; 570/178, 570/177

[56] References Cited

U.S. PATENT DOCUMENTS

| | | | |
|---|---|---|---|
| 3,152,051 | 10/1964 | Fainberg et al. | 570/178 |
| 3,689,373 | 9/1972 | Hutchinson | 570/178 |
| 3,689,374 | 9/1972 | Hanson | 570/178 |
| 3,692,635 | 9/1972 | Fozzard | 203/62 |
| 3,732,150 | 5/1973 | Bailey | 570/178 |
| 4,950,364 | 8/1990 | Wismer | 570/178 |
| 4,975,156 | 12/1990 | Wismer | 203/67 |

FOREIGN PATENT DOCUMENTS 45-32681 10/1970 Japan.

Primary Examiner—Wilbur Bascomb, Jr.
Attorney, Agent, or Firm—James J. Flynn

[57] ABSTRACT

Separating pentafluoroethane from a mixture of pentafluoroethane and chloropentafluoroethane by adding a fluorocarbon extractive agent having 1–4 carbon atoms, and optionally containing hydrogen and/or chlorine, in an extractive distillation zone to recover pentafluoroethane substantially free of chloropentafluoroethane in the overhead product stream.

9 Claims, No Drawings

PROCESS FOR SEPARATING PENTAFLUOROETHANE FROM A MIXTURE OF HALOGENATED HYDROCARBONS CONTAINING CHLOROPENTAFLUOROETHANE

BACKGROUND OF THE INVENTION

This invention is directed to a process for separating pentafluoroethane from a mixture of pentafluoroethane (HFC-125) and chloropentafluoroethane (CFC-115) by extractive distillation.

New regulations have been designed to protect the ozone layer from possible damage by fully halogenated chlorofluorocarbons. Pentafluoroethane (HFC-125) is a valuable non-chlorine containing fluorocarbon that is especially useful as a refrigerant, blowing agent, propellant, fire extinguishing agent or sterilant carrier gas. Pentafluoroethane is usually prepared by chlorofluorinating perclene to produce a mixture of 1,1,2-trichlorotrifluoroethane (CFC-113), 1,2-dichlorotetrafluoroethane (CFC-114) and 2,2-dichloro-1,1,1-trifluoroethane (HCFC-123). After removal of 1,1,2-trichlorotrifluoroethane, the remaining mixture can be fluorinated by various processes, resulting in a mixture containing pentafluoroethane (HFC-125) and chloropentafluoroethane (CFC-115), and smaller amounts of other fluorinated compounds, e.g., hexafluoroethane (FC-116). Various other methods for making pentafluoroethane together with chloropentafluoroethane are known and the resulting mixture made by other processes can likewise be treated by the extractive distillation process of the present invention to recover pentafluoroethane. Unfortunately, the mixture of pentafluoroethane and chloropentafluoroethane form a near-azeotrope. The boiling points of the halogenated hydrocarbons are very close, −48.5° C. for pentafluoroethane and −38.7° C. for chloropentafluoroethane, and their relative volatility is below 1.1 at concentrations of pentafluoroethane greater than 87.5 mole %, and below 1.01 at concentrations above 95 mole %. The boiling point and relative volatilities indicate that it would be extremely difficult, if not impossible, to recover substantially pure pentafluoroethane from such mixtures by simple distillation and, therefore, extractive distillation is an alternative procedure that could possibly be used. However, the main problem employing an extractive distillation process is discovering an extraction agent which will sufficiently aid the desired separation process to make up for the need to add a new separation step to remove and recycle the extractive agent. Methods which have been used to predict what extractive agents are likely to work have been described by L. Berg in *Chem. Eng. Progress*, Vol. 65, No. 9, pages 52–57, September 1969. In discussing extractive distillation, it is stated in the article that "hydrogen bonds appear to be an important factor since all successful extractive distillation agents are highly hydrogen bonded liquids . . . Thus, the criteria for successful extractive agents are that they boil considerably higher than the compounds being separated, form no minimum azeotropes with the components, and be a highly hydrogen bonded liquid, that is, Class I or Class II of the hydrogen bond classification. Phenols, aromatic amines (aniline and its derivatives), higher alcohols, glycols, etc. are examples of successful extractive agents." The present invention makes possible separation of pentafluoroethane from chloropentafluoroethane by extractive distillation with compounds that however, are not highly hydrogen bonded.

SUMMARY OF THE INVENTION

The present invention relates to a process for separating pentafluoroethane from a first mixture of pentafluoroethane and chloropentafluoroethane which comprises:

adding a fluorocarbon extractive agent having 1–4 carbon atoms optionally containing hydrogen and/or chlorine and having a boiling point greater than −39° C., preferably greater than −12° C., and less than about 50° C., to the first mixture in order to form a resultant second mixture; and separating pentafluoroethane from chloropentafluoroethane of the second mixture by extractively distilling the second mixture in an extractive distillation zone and thereby recovering as overhead product, a pentafluoroethane stream substantially free of chloropentafluoroethane.

The extractive agent used in the present invention is closely related chemically to the pentafluoroethane being separated from the mixture of fluorinated hydrocarbons which advantageously minimizes the risk of introducing completely extraneous impurities in the fluorinated hydrocarbon being separated. The extractive agent can be readily removed from the stream containing chloropentafluoroethane by simple distillation for reuse in the system.

Representative fluorocarbon agents suitable for use in this process are fluorocarbons, including chlorofluorocarbons, that optionally contain hydrogen. Specific examples of such fluorocarbons include 1,2-dichlorotetrafluoroethane (CFC-114), 1,1-dichlorotetrafluoroethane (CFC-114a), 1,1,2-trichlorotrifluoroethane (CFC-113), 1,1,1-trichlorotrifluoroethane (CFC-113a), 2-chloro-1,1,1,2-tetrafluoroethane (HCFC-124), 2,2-dichloro-1,1,1-trifluoroethane (HCFC-123), trichlorofluoromethane (CFC-11), and octafluorocyclobutane (FC-C318).

DETAILED DESCRIPTION OF THE INVENTION

The mixture of pentafluoroethane and chloropentafluoroethane in their separated and pure state which are the primary constituents of the first mixture have boiling points of −48.5° C. and −38.7° C., respectively. The relative volatilities at atmospheric pressure of pentafluoroethane/chloropentafluoroethane was found to be nearly 1.0 as 100% purity of pentafluoroethane is approached. These data indicate that using conventional distillation procedures will not result in the separation of a substantially pure compound because of the close boiling points and the low value of relative volatility of the compounds.

To determine the relative volatility of pentafluoroethane and chloropentafluoroethane the so-called PTx Method was used, based upon the Wilson equation, as described in the 6th Edition of Perry's "Chemical Engineers, Handbook" on pages 4–76 and 4–77. In this procedure, the total pressure in a cell of known volume is measured at a constant temperature for various known charge compositions of the binary pair. This information can be reduced to equilibrium vapor and liquid compositions in the cell by sue of an equation of state to model vapor pressure non-idealities and an activity coefficient equation to model liquid phase non-idealities. The basic premise in this procedure is that both the equation of state and the activity coefficient equation can adequately predict the behavior of the system.

The results of PTx measurements and the above series of calculations are summarized in Tables 1 through 3, giving results for −25° C., 0° C. and 25° C.

TABLE 1

Vapor-Liquid Measurements on the HFC-125/CFC-115 System at −25° C.

| Mole %, CFC-115 | | | Pressure, psia | | Relative Volatility |
|---|---|---|---|---|---|
| Charge | Liquid | Vapor | Meas. | Calc. | HFC-125/CFC-115 |
| 17.67 | 17.72 | 15.84 | 40.75 | 40.75 | 1.145 |
| 13.48 | 13.51 | 12.34 | 40.75 | 40.95 | 1.109 |
| 10.40 | 10.42 | 9.69 | 40.95 | 41.06 | 1.084 |
| 7.40 | 7.42 | 7.02 | 41.10 | 41.15 | 1.060 |

TABLE 2

Vapor-Liquid Measurements on the HFC-125/CFC-115 System at 0° C.

| Mole %, CFC-115 | | | Pressure, psia | | Relative Volatility |
|---|---|---|---|---|---|
| Charge | Liquid | Vapor | Meas. | Calc. | HFC-125/CFC-115 |
| 17.67 | 17.78 | 15.97 | 96.95 | 97.14 | 1.138 |
| 13.48 | 13.55 | 12.43 | 97.20 | 97.65 | 1.104 |
| 10.40 | 10.45 | 9.75 | 98.00 | 97.94 | 1.080 |
| 7.40 | 7.43 | 7.06 | 98.00 | 98.16 | 1.057 |

TABLE 3

Vapor-Liquid Measurements on the HFC-125/CFC-115 System at 25° C.

| Mole %, CFC-115 | | | Pressure, psia | | Relative Volatility |
|---|---|---|---|---|---|
| Charge | Liquid | Vapor | Meas. | Calc. | HFC-125/CFC-115 |
| 17.67 | 17.87 | 16.36 | 198.60 | 198.63 | 1.113 |
| 13.48 | 13.61 | 12.66 | 200.25 | 199.72 | 1.087 |
| 10.40 | 10.49 | 9.88 | 200.75 | 200.37 | 1.068 |
| 7.40 | 7.45 | 7.12 | 201.00 | 200.87 | 1.051 |

While HFC-125 has a good relative volatility vs. CFC-115 at low concentrations, the relative volatility is nearly 1.0 as 100% purity of HFC-125 is approached. This would make it most difficult or impossible to remove substantially all the pentafluoroethane by conventional distillation from such a mixture.

The technique of extractive distillation is well-known in the art. Extractive distillation depends on the ability of certain extractive agents to increase the relative volatility of the binary pair of compounds to be separated. This operation is generally carried out in a continuous distillation column, comprising a multi-stage distillation column with a minimum of two feed points, a reboiler and an overhead condenser for returning reflux to the column. The extractive agent, e.g., 1,2-dichlorotetrafluoroethane (CFC-114), is fed to an upper feed point of the fractionating column and the mixture requiring separation, i.e., pentafluoroethane and chloropentafluoroethane, is fed to a lower feed point of the column. The extractive agent passes downward as a liquid through trays in the column to the bottom. The pentafluoroethane being more volatile than the chloropentafluoroethane in the presence of the extractive agent passes substantially free of chloropentafluoroethane from the top of the column where it is condensed, part returned as reflux and the remainder recovered. To obtain a substantially pure pentafluoroethane, frequently quantities of hexafluoroethane may also then be removed from the overhead product stream. This removal of hexafluoroethane and recovery of substantially pure pentafluoroethane can be accomplished by simple distillation. The bottoms from the kettle containing chloropentafluoroethane and the extractive agent is passed to a stripper or distillation column for conventional separation of the components and recycle of the extractive agent.

The required diameter and number of separation stages in the column for extractive distillation, the reflux ratio and optimum column temperatures and pressures are readily calculable by those skilled in the art with the data on relative volatilities, vapor pressure and physical constants for the individual components and their mixtures. The following Examples illustrate specific embodiments of the present invention wherein parts are by weight unless otherwise indicated.

EXAMPLE 1

The separation of pentafluoroethane from a mixture of pentafluoroethane and chloropentafluoroethane was accomplished as follows:

The extractive distillation column used was designed to accommodate 72 theoretical stages by using Goodloe packing with the height equivalent to a theoretical plate of 9 inches. The extractive distillation column was constructed of 8-inch schedule 40 stainless steel pipe flanged every 8 feet to allow placement of 6 vapor-liquid redistributors. Two feed locations were designated, one of which supplied the extractive agent on theoretical stage 9, and the second feed location supplied the mixture to be separated on theoretical stage 48. Pressure in the column was 150 psia (1034 Kpa).

A feed stock mixture of, by weight, 6.55% pentafluoroethane (HFC-125), 85.46% chloropentafluoroethane (CFC-115), 0.44% hexafluoroethane (FC-116) and 7.55% of 1,2-dichlorotetrafluoroethane (CFC-114) was fed to the distillation column at theoretical stage 48, at a temperature of 20° C. The fluorocarbon extractive agent CFC-114 was fed to the column at theoretical stage 9, at 20° C.

The following results were obtained.

| | Material Balance Stated in Percent and Kg/Hr | | | |
|---|---|---|---|---|
| Component | Feed | Extractive Agent | Distillate | Bottoms |
| FC-116 | 0.44% | 0.00 | 8.14% | 0.00 |
| HFC-125 | 6.55% | 0.00 | 91.58% | 0.67% |
| CFC-115 | 85.46% | 0.00 | 0.28% | 34.93% |
| CFC-114 | 7.55% | 100.00% | 0.00 | 64.40% |
| Total Flow kg/Hr | 150 | 225 | 9 | 365 |

On a HFC-125/CFC-115 basis with FC-116 removed by simple distillation, the HFC-125 in the distillate is 99.695%.

EXAMPLE 2

The procedure described above in Example 1 was substantially repeated using as the extractive agent CFC-114 except that the feed stock had the following composition, by weight: 10.48% pentafluoroethane (HFC-125), 39.62% chloropentafluoroethane (CFC-115), 2.93% hexafluoroethane (FC-116) and 46.97% 1,2-dichlorotetrafluoroethane (CFC-114).

The following results were obtained.

| Component | Feed | Extractive Agent | Distillate | Bottoms |
|---|---|---|---|---|
| FC-116 | 2.93% | 0.00 | 23.73% | 0.00 |
| HFC-125 | 10.48% | 0.00 | 76.17% | 0.31% |
| CFC-115 | 39.62% | 0.00 | 0.10% | 23.19% |
| CFC-114 | 46.97% | 100.00% | 0.00 | 76.50% |
| Total Flow kg/hr | 275 | 230 | 35 | 470 |

On a HFC-125/CFC-115 basis with FC-116 removed by simple distillation, the purity of the HFC-125 in the distillate is 99.872%.

ADDITIONAL EMBODIMENTS

Established methods of distillation calculations permit us to properly extend the extractive distillation process of the present invention to other fluorocarbon extractive agents having 1-4 carbon atoms, optionally containing either hydrogen or chlorine atoms or both. For the following embodiments, 1,1-dichlorotetrafluoroethane (CFC-114a) and 2-chloro-1,1,1,2-tetrafluoroethane (HCFC-124), the vapor-liquid equilibrium was determined for the extractive agents relative to HFC-125 and CFC-115. Assuming a distillation column of the design used in Example 1 herein, the minimum flow rate of the fluorocarbon extractive agent was calculated for achieving a 99.90% purity for HFC-125 from the feed composition specified in Table 4.

TABLE 4

| | | Minimum Flowrate in Kg per 100 Kg/Feed | | | |
|---|---|---|---|---|---|
| Extractive Agent | Reflux Ratio | 98.50% Purity HFC-125 | 99.00% Purity HFC-125 | 99.25% Purity HFC-125 | 99.50% Purity HFC-125 |
| CFC-114 | 5 | 109.55 | 100.04 | 92.72 | 87.35 |
| CFC-114a | 5 | 108.47 | 99.30 | 91.94 | 80.60 |
| HCFC-124 | 8 | 331.34 | 294.81 | 267.28 | 229.16 |

From the above, it can be seen that the use of the fluorocarbon extractive agent CFC-114a shows almost identical results to the use of the fluorocarbon extractive agent CFC-114 in the present extractive distillation process. However, when HCFC-124 is used as the extractive agent, a higher reflux ratio and greater feed rate is required to achieve the same purity for HFC-125.

If the actual vapor-liquid equilibrium data are not available for other extractive agents of the present invention, it can be assumed that all the ingredients behave as ideal mixtures except for the HFC-125/CFC-115 binary pair. Using this assumption, and calculating the feed rate of the fluorocarbon extractive agent necessary to purify a 90.00% HFC-125/1.00% CFC-115 mixture to 99.90% as in the previous Table, the following results were obtained.

| | Minimum Flowrate in Kg per 100 Kg/Feed | |
|---|---|---|
| Extractive Agent | Reflux Ratio | 99.00% Purity HFC-125 |
| CFC-11 | 10 | 304.82 |
| CFC-113 | 10 | 399.62 |
| CFC-113a | 10 | 400.13 |
| HCFC-123 | 10 | 330.89 |
| FC-C318 | 10 | 350.79 |

The above shows that other fluorocarbon extractive agents as defined herein having 1-4 carbon atoms are effective for the separation of HCFC-125 from CFC-115.

I claim:

1. A process for separating pentafluoroethane from a first mixture of pentafluoroethane and chloropentafluoroethane which comprises:

adding a fluorocarbon extractive agent having 1-4 carbon atoms optionally containing hydrogen and/or chlorine, and having a boiling point greater than −39° C., and less than about 50° C., to the first mixture in order to form a resultant second mixture;

separating pentafluoroethane from chloropentafluoroethane of the second mixture by extractively distilling the second mixture in an extractive distillation zone and thereby recovering, as overhead product, a pentafluoroethane stream substantially free of chloropentafluoroethane.

2. A process of claim 1 wherein the extractive agent is 1,2-dichlorotetrafluoroethane.

3. A process of claim 1 wherein the extractive agent is 1,1-dichlorotetrafluoroethane.

4. A process of claim 1 wherein the extractive agent is 2-chloro-1,1,1,2-tetrafluoroethane.

5. A process of claim 1 wherein the extractive agent is 2,2-dichloro-1,1,1-trifluoroethane.

6. A process of claim 1 wherein the extractive agent is 1,1,2-trichlorotrifluoroethane.

7. A process of claim 1 wherein the extractive agent is 1,1,1-trichlorotrifluoroethane.

8. A process of claim 1 wherein the extractive agent is trichlorofluoromethane.

9. A process of claim 1 wherein the extractive agent is octafluorocyclobutane.

* * * * *